(12) United States Patent
Farahmand

(10) Patent No.: US 6,406,419 B1
(45) Date of Patent: Jun. 18, 2002

(54) EYEGLASS COMBINATION WITH PERMANENT MAGNETS

(76) Inventor: Salar Farahmand, 16661 Ventura Bvd. Suite 403, Encino, CA (US) 91436

( * ) Notice: Subject to any disclaimer, the term of this patent is extended or adjusted under 35 U.S.C. 154(b) by 0 days.

(21) Appl. No.: 09/535,454

(22) Filed: Mar. 24, 2000

Related U.S. Application Data

(60) Provisional application No. 60/126,136, filed on Mar. 25, 1999.

(51) Int. Cl.$^7$ .............................. A61N 1/00; G02C 1/00
(52) U.S. Cl. ......................................... 600/15; 351/158
(58) Field of Search ........................... 600/15; 351/158, 351/52, 157, 123; 72/189; 2/431

(56) References Cited

U.S. PATENT DOCUMENTS

| | | | | |
|---|---|---|---|---|
| 2,920,327 A | * | 1/1960 | Singer | 2/431 |
| 3,583,192 A | * | 6/1971 | Kocks | 72/189 |
| 4,070,103 A | * | 1/1978 | Meeker | 351/52 |
| 4,988,181 A | * | 1/1991 | Riach, Jr. | 351/52 |
| 5,096,284 A | * | 3/1992 | NakaMats | 351/123 |
| 5,120,119 A | * | 6/1992 | Mats | 351/157 |
| 5,181,051 A | * | 1/1993 | Townsend et al. | 351/52 |
| 5,389,981 A | * | 2/1995 | Riach, Jr. | 351/158 |
| 6,053,859 A | * | 4/2000 | Hanglund | 600/15 |

* cited by examiner

*Primary Examiner*—Kevin Shaver
*Assistant Examiner*—Nikita R Veniaminov
(74) *Attorney, Agent, or Firm*—Walter Unterberg

(57) ABSTRACT

This invention relates to the use of permanent magnets to improve the condition of the eyes, such as to provide relaxation, overcome tiredness, and create good feeling in the eyes. It is a combination of bi-polar magnets and eyeglasses in which circular magnets are mounted concentrically into the rims of eyeglasses and so placed immediately in front of the eyes for an optimum therapeutic effect. The magnets are solid cylinders with a large central hole mounted on intact or perforated eyeglass lenses; or thin flexible disks with either a large central hole or a plurality of small holes mounted directly on the eyeglass rims in place of lenses. The magnets, available commercially, are all bi-polar and vary in field strength from 400 to 1000 gauss. The use of the magnet-eyeglass combination should be from 10 to 20 minutes once or twice a day for an improvement in the eyes.

18 Claims, 2 Drawing Sheets

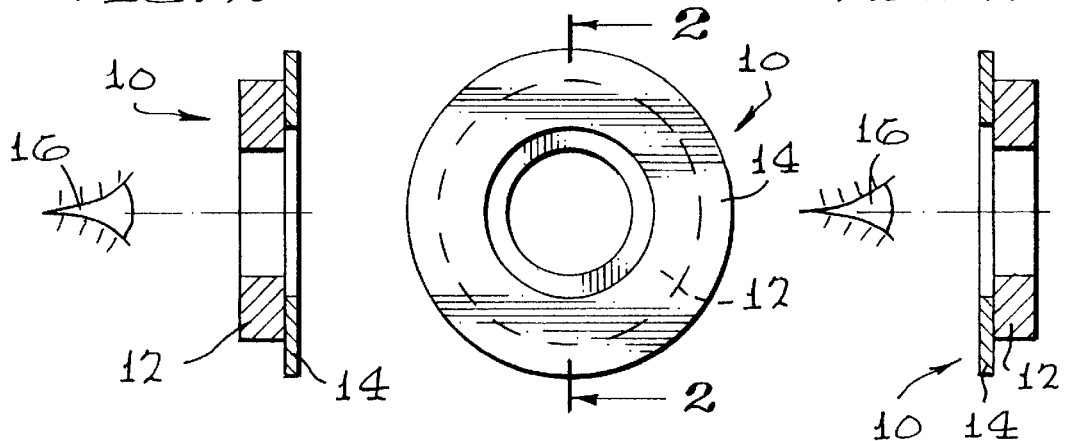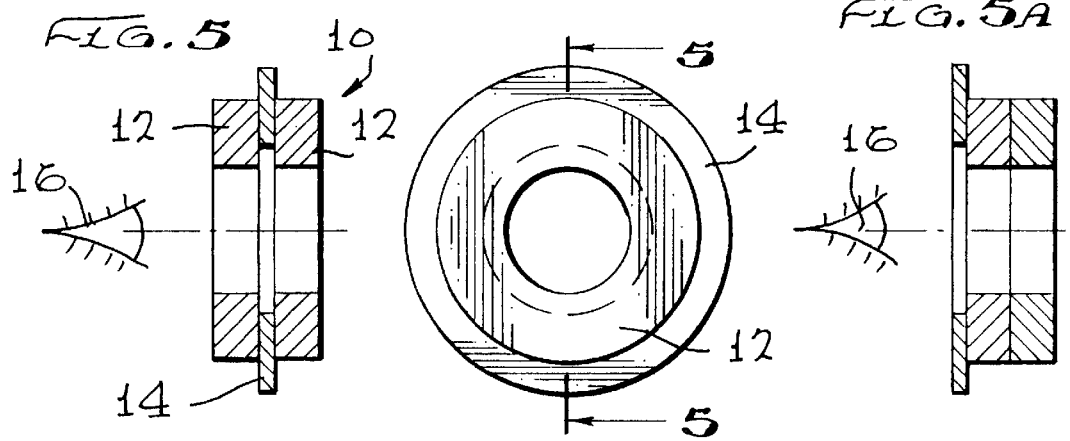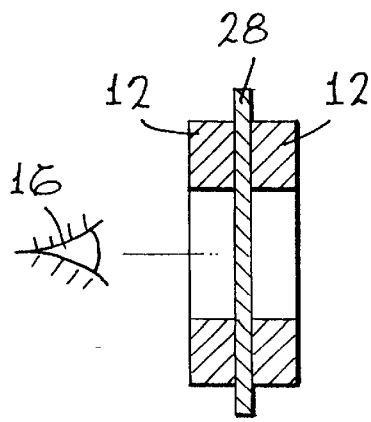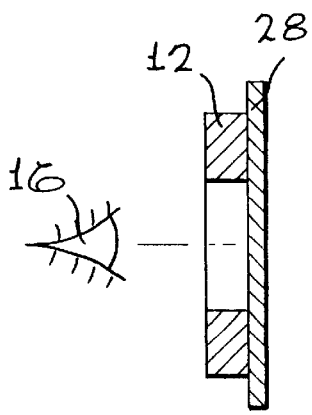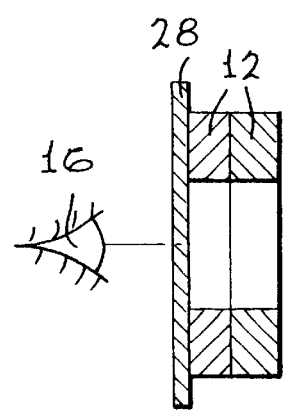

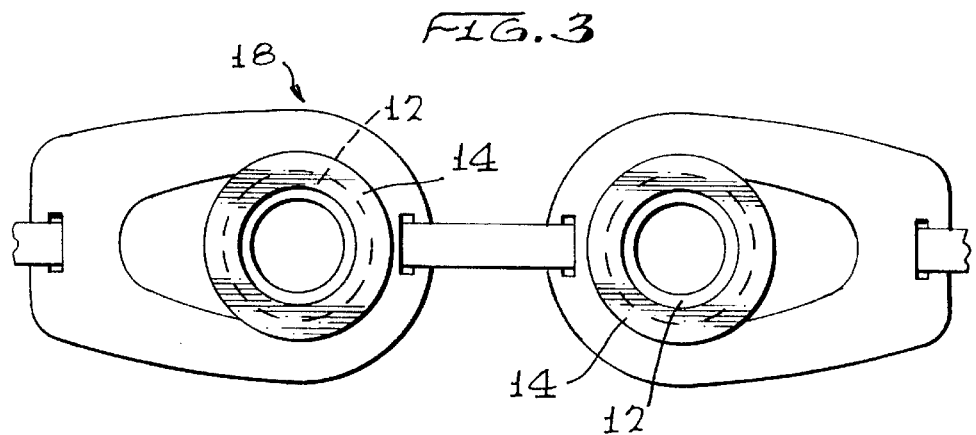
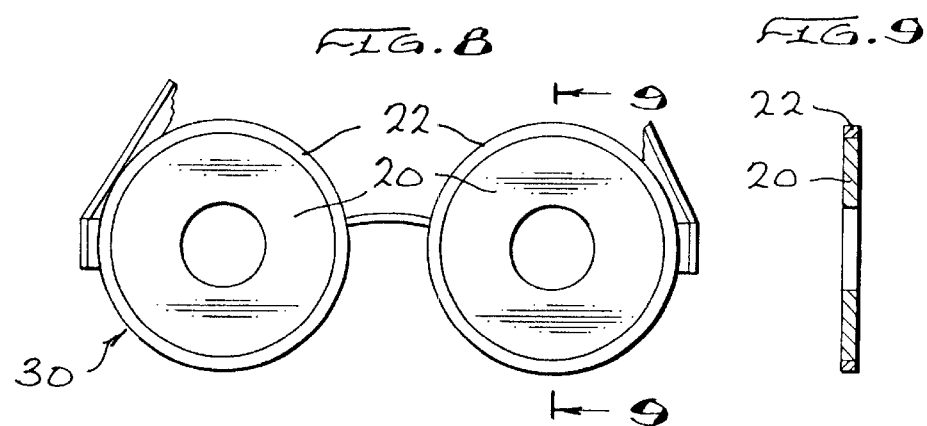
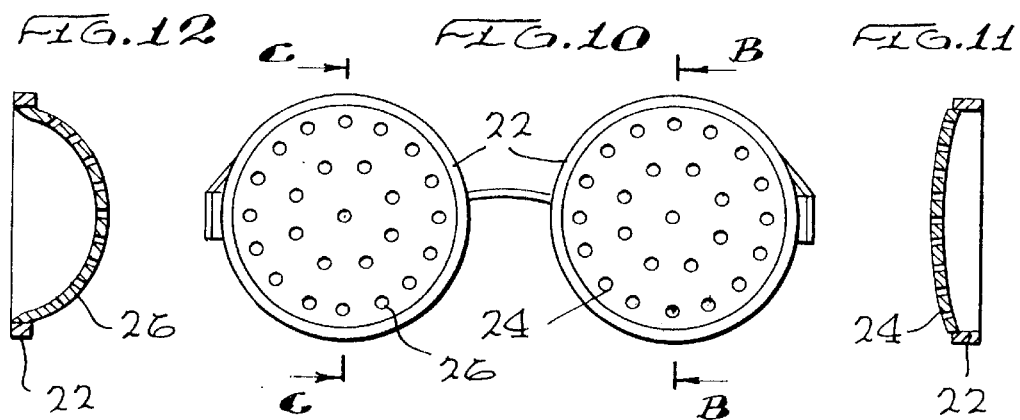

EYEGLASS COMBINATION WITH PERMANENT MAGNETS

CROSS-REFERENCE TO RELATED APPLICATIONS

This application claims the benefit of Provisional Patent Application Ser. No. 60/126,136 filed Mar. 25, 1999.

BACKGROUND OF THE INVENTION

1. Field of the Invention

This invention relates generally to the field of using permanent magnet devices to provide magnetic energy to heal the human body of afflictions. More particularly, it relates to the application of permanent magnets to improve the condition of the eyes, such as to provide relaxation, overcome tiredness, and create good feeling in the eyes.

2. Discussion of Related Art

Permanent magnets have a remarkable ability to work with A almost any other treatment modality to reinforce it by providing a synergistic effect. However, permanent magnets work well by themselves, too.

The most common use of magnets is for pain relief, for which naturally charged permanent magnets have been used since antiquity. In 1997, Baylor University College of Medicine conducted a study using modern magnets that were naturally charged to high field strengths. The results of this study gave credibility to the use of externally charged permanent magnets in the treatment of pain. There is an improvement when such magnets are applied to humans, e.g., in devices to accelerate the healing of human bones. Magnets also find use in Magnetic Resonance Imaging (MRI), where a large circular magnet determines the magnetic bearings of a number of atom nuclei in the patient's body.

A strong opinion in current permanent magnet application maintains that the negative or north-seeking pole produces the greatest benefit and is the safest polarity to use. This is combined with the belief that the earth's magnetic field is an essentially negative field and that the polarity of normal human cells is negative, but that illness changes it to positive.

Therefore, to reverse this condition negative poles are used in proximity to the subject, and furthermore, the effect is believed to become stronger as the magnetic flux density is increased. This leads to-use of the strongest possible magnetic poles.

There have, however, been indications that application of purely negative pole magnetism does not achieve the best effect regardless of pole strength. The present invention overcomes this deficiency by the use of permanent magnets with both negative and positive polarities.

In the application of magnets to the human eye there exist plastic frame spectacles with small magnets embedded in the bridge and rims of the frame. Such peripheral magnets are not close enough to the eye to exercise a beneficial effect.

The present invention has for its object an improvement on the use of peripheral magnets for the human eye. The invention provides permanent magnets with dual polarity immediately in front of the eye, in combination with eye glasses.

BRIEF SUMMARY OF THE INVENTION

This invention is a combination of bi-polar permanent magnets and eyeglasses in which magnets with generally circular peripheries are placed concentrically into the rims of a pair of eye glasses. In this way the magnets are mounted immediately in front of the eyes for an optimum effect. The matching eyeglasses (spectacles or goggles) can have circular rims.

The magnets are of two types: (1) solid cylinders with a single large central coaxial hole, and (2) thin flexible circular disks with a single large central hole or a plurality of small holes uniform over the disk. In case (1) one of the two opposite flat faces is a negative pole and the other a positive pole. In case (2) with a single large central hole, too, one flat face is a, negative pole and the opposite face is a positive pole. In case (2) with a plurality of small holes there are alternating negative and positive poles throughout the area of the disk magnet.

In case (1) the cylinder magnet is mounted centrally on the transparent eyeglass lens which can remain intact so that the eye looks out through the lens material; or the lens may be perforated with a central circular hole, so that the magnet is mounted on the lens periphery and the eye looks out through air in the center.

For closeness to the eye, the cylinder magnet is mounted on the inside of the lens facing the eye. For a greater effect a second identical cylinder magnet is placed on the outside of the lens in line with the first magnet. In this arrangement the poles on the magnet faces next to the lens are unlike,i.e., one negative and one positive, so that they attract each other and the second, outside, magnet will stay in place without any structural attachment. Alternatively, either a single magnet, or a pair of magnets attached to each other by magnetic force (as above), can be mounted on the side of the lens facing away from the eye.

In case (2) the circular disk magnets are mounted on the circular rims in place of the eyeglass lenses. With the single large circular hole, the disk is flat or slightly curved. With the plurality of small holes, the disk is oversize to accommodate a small or large curvature symmetrically around the center. The curvature assists the structural integrity of the magnet-eyeglass combination.

The magnet material can be ferrite, ceramic or a rare earth alloy, such as neodymium iron boron. The magnetic field strength varies from 400 to 1000 gauss. The magnets for this invention are commercially available from supply houses such as OMS Medical Supplies, Braintree, Mass.; Nikken Company, Irvine, Calif.; or Magnet Sales and Manufacturing Inc., Culver City, Calif. The flexible disk magnets are available with a gold foil covering.

The outer diameters of the magnets must fit within the selected eyeglass rim diameters and range typically from about 1.15 inch to about 2.0 inch. For type (1), the hole diameters range typically from about 0.3 inch (400 gauss) to about 0.7 inch (1000 gauss); and the the axial width typically from about 0.2 inch to about 0.4 inch. For type (2), the sheet thickness ranges typically from about 0.07 inch to 0.08 inch; the single hole diameter ranges typically from about 0.3 inch to about 0.7 inch; and the multiple hole diameter typically from about 0.05 inch to about 0.08 inch.

When a subject wears this eyeglass combination with permanent magnets, magnetic flux is conducted into the musculature of the eyes and to the eyes themselves to counteract tiredness of the eyes, relax the eyes, and provide good feeling to the eyes.

The use of the glasses should be from 10 to 20 minutes, once or twice a day, such as once in the morning and once in the evening. The eyeglass-magnet combination can be worn while walking at home, sitting and reading, watching television, with eyes closed or in bed before sleeping or after waking.

Additional benefits from such use of the eyeglass-magnet combination may include improved vision because the eyes become more relaxed and energized, possibly by increased circulation of the blood. Also, there may occur improvement in eye disorders, such as myopia, glaucoma, cataracts, dryness, watery eyes, and difficulty in driving at night.

BRIEF DESCRIPTION OF THE SEVERAL VIEWS OF THE DRAWING

A better understanding of the invention may be gained by reference to the Detailed Description which follows, in conjunction with 12 drawing figures showing different views of various embodiments of the invention. In the drawing FIG. 1 is a front view looking at the eye of the perforated eyeglass lens—solid magnet combination with the magnet mounted on the side of the lens facing the eye;

FIG. 2 is a sectional side view of the combination of FIG. 1 taken on line 2—2 in FIG. 1;

FIG. 2A is a sectional side view like FIG. 2, but with the magnet mounted on the side of the lens facing away from the eye;

FIG. 3 is a front view looking at the eyes of swimming goggles combined with solid magnets on the eye side as in FIG. 1 and FIG. 2;

FIG. 4 is a front view looking at the eye of the perforated eyeglass lens—solid magnet combination with two magnets, one on either side of the lens;

FIG. 5 is a sectional side view of the combination of FIG. 4 taken on line 5—5 in FIG. 4;

FIG. 5A is a sectional side view like FIG. 5, but with both magnets on the side of the lens facing away from the eye.

FIG. 6 is a sectional side view like FIG. 2, but with intact eyeglass lens;

FIG. 7 is a sectional side view like FIG. 5, but with intact instead of perforated eyeglass lens;

FIG. 7A is a sectional side view like FIG. 5A, but with an intect instead of perforated eyeglass lens;

FIG. 8 is a front view looking at the eyes of a metal rim frame—flat flexible single hole magnet combination;

FIG. 9 is a sectional side view of the combination of FIG. 8 taken on line 9—9 in FIG. 8;

FIG. 10 is a front view looking at the eyes of a metal rim frame—curved flexible multiple-hole magnet combination;

FIG. 11 is a sectional side view of the combination of FIG. 10 taken on line B—B in FIG. 10 showing a small-curvature magnet; and FIG. 12 is a sectional side view of the combination of FIG. 10 taken on line C—C showing a large-curvature magnet.

DETAILED DESCRIPTION OF THE INVENTION

Referring now to FIG. 1 and FIG. 2, the combination 10 of a solid permanent magnet 12 with a perforated eyeglass lens 14 is shown, together with location of the human eye 16. Magnet 12 is bi-polar with a negative pole on one flat face and a positive pole pole on the opposite flat face. Magnet 12 is mounted concentrically on the periphery of perforated lens 14 on the side facing eye 16. Because of the central perforation, or large central hole, in lens 14 and the central hole in magnet 12, eye 16 has an uninterrupted view of the environment. Alternatively, as shown in FIG. 2A, magnet 12 can be mounted on the side of perforated lens 14 facing away from eye 16.

Referring now to FIG. 3, there is shown an application of the combination 10 of FIG. 1 and FIG. 2 to a pair of swimming goggles 18 in front view. Goggle lenses 14 are perforated just as in FIG. 1 and FIG. 2, and magnets 12 with central holes are mounted on the lens sides facing the eyes, which have an uninterrupted view of the environment.

Referring now to FIG. 4 and FIG. 5, there is shown the combination 10 with two magnets 12, one on each side of perforated lens 14, with the inner magnet 12 facing eye 16. While inner magnet 12 is mounted on perforated lens 14, outer magnet 12 is kept in position by magnetic force. This is arranged by having the pole on the inner face of outer magnet 12 unlike the pole on the outer face of inner magnet 12, i.e., one negative and one positive, so that the magnets attract each other. The net effect is a doubling of the magnetic flux to the eye. Alternatively, as shown in FIG. 5A, a first magnet 12 can be mounted on the outside face of lens 14, and a second magnet 12 can be attached to first magnet 12 by magnetic force.

Referring now to FIG. 6, this is a sectional view comparable to FIG. 2, but with an intact transparent eyeglass lens 28. In this case eye 16 views the environment through transparent intact lens 28, which acts to protect the eye. This is also an option when the eyeglasses have corrective lenses 28.

Referring now to FIG. 7, this is a sectional view comparable to FIG. 5, but with an intact transparent eyeglass lens 28. The feature of having two magnets 12 is retained, but the eye views the environment through transparent intact lens 28 which acts to protect the eye. This also an option when the eyeglasses have corrective lenses 28. Alternatively, as shown in FIG. 7A, a first magnet 12 can be mounted on the outside face of lens 28 and a second magnet 12 attached to first magnet 12 by magnetic force.

While FIG. 1–FIG. 7A have illustrated the combination with permanent solid magnets with a central hole mounted on eyeglass lenses, the remaining figures, FIG. 8–FIG. 12, show the combination with disk-like permanent flexible magnets mounted in place of eyeglass lenses. A flexible magnet can have a single large central hole or a plurality of small uniformly distributed holes.

Referring now to FIG. 8 and FIG. 9, there is shown combination 30 of a wire rim frame 22 with a flat flexible disk permanent magnet with large central hole 20. Magnets 20 are mounted in rims 22 in place of eyeglass lenses. Here one flat face of magnet 20 has negative polarity and the opposite face has positive polarity.

Referring now to FIG. 10, FIG. 11 and FIG. 12, there is shown combination 32 of wire rim frame 22 with a curved flexible disk permanent magnet with a plurality of uniformly distributed small holes 24 (small curvature) or 26 (large curvature). The curvature assists the structural integrity of combination 32. In magnets 24 and 26 there are alternating negative and positive poles throughout the area of the disk.

The magnet material can be ferrite, ceramic or a rare earth alloy, such as neodymium iron boron. The magnetic field strength varies from 400 to 1000 gauss. The magnets for this invention are commercially available from supply houses such as OMS Medical Supplies, Braintree, Mass.; Nikken Company, Irvine, Calif.; or Magnet Sales and Manufacturing Inc., Culver City, Calif. The flexible disk magnets are available with a gold foil covering.

The outer diameters of the magnets must fit within the selected eyeglass rim diameters and range typically from about 1.15 inch to about 2.0 inch. For type (1), the hole diameters range typically from about 0.3 inch (400 gauss) to about 0.7 inch (1000 gauss); and the the axial width typically from about 0.2 inch to about 0.4 inch. For type (2), the sheet thickness ranges typically from about 0.07 inch to 0.08 inch; the single hole diameter ranges typically from about 0.3 inch to about 0.7 inch; and the multiple hole diameter typically from about 0.05 inch to about 0.08 inch.

When a subject wears this eyeglass combination with permanent magnets, magnetic flux is conducted into the musculature of the eyes and to the eyes themselves to counteract tiredness of the eyes, relax the eyes, and provide good feeling to the eyes.

The use of the glasses should be from 10 to 20 minutes, once or twice a day, such as once in the morning and once in the evening. The eyeglass-magnet combination can be worn while walking at home, sitting and reading, watching television, with eyes closed or in bed before sleeping or after waking.

Additional benefits from such use of the eyeglass-magnet combination may include improved vision because the eyes become more relaxed and energized, possibly by increased circulation of the blood. Also, there may occur improvement in eye disorders, such as myopia, glaucoma, cataracts, dryness, watery eyes, and difficulty in driving at night.

It is to be understood-that the invention may be realized with embodiments differing from the specific apparatus illustrated herein without departing from the scope of the present invention as delineated in the following claims.

What is claimed is:

1. An eyeglass combination with permanent magnets for improvement of the eyes, said combination comprising:
    an eyeglasses frame;
    a pair of transparent lenses set in said eyeglasses frame; and
    a pair of bi-polar permanent magnets mounted concentrically on said pair of lenses immediately in front of the eyes, each said magnet of said pair of magnets being a solid cylinder with a central axial-hole, having a negative pole on one flat face and a positive pole on an opposing flat face,
    said permanent magnets providing the therapeutic effect of increasing the flow and oxygen-carrying capacity of the blood circulating in the region of the eyes and activating the minerals in the cells and tissues of the eyes and surrounding region.

2. The combination of claim 1 wherein the eyeglasses are spectacles.

3. The combination of claim 1 wherein the eyeglasses are goggles.

4. The combination of claim 1 further comprising a second pair of bi-polar magnets coaxial with, adjacent to and attached to said pair of magnets by magnetic force due to adjacent magnet faces having unlike poles, one negative and one positive, for a greater said effect.

5. The combination of claim 1 wherein each lens in said pair of lenses is perforated with a central hole around which each magnet of said pair of magnets is mounted.

6. The combination of claim 5 further comprising a second pair of bi-polar magnets coaxial with, adjacent to and attached to said pair of magnets by magnetic force due to adjacent magnet faces having unlike poles, one negative and one positive, for a greater said effect.

7. The combination of claim 1 wherein each said magnet in said pair of permanent magnets has a field strength in the range of 400 to 1000 gauss and is fabricated from a material selected from the group consisting of ferrite, ceramic and neodymium iron boron.

8. The combination of claim 1 wherein said magnets have ranges in cylinder outer diameter from about 1.15 inch to about 2.0 inch, in hole diameter from about 0.3 inch to about 0.7 inch, and in axial width from about 0.2 inch to about 0.4 inch.

9. An eyeglass combination with permanent magnets for improvement of the eyes, said combination comprising:
    an eyeglasses frame; and
    a pair of bi-polar permanent magnets mounted directly on rims of said eyeglasses frame immediately in front of the eyes, each said magnet of said pair of magnets being a circular disk-shaped flexible permanent magnet with a large central hole, having a negative pole on one flat face and a positive pole on an opposite flat face,
    said permanent magnets providing the therapeutic effect of increasing the flow and oxygen-carrying capacity of the blood circulating in the region of the-eyes and activating the minerals in the cells and tissues of the eyes and surrounding region.

10. The combination of claim 7 wherein the eyeglasses are spectacles.

11. The combination of claim 7 wherein the eyeglasses are goggles.

12. The combination of claim 7 wherein each said magnet in said pair of permanent magnets has a field strength in the range of 400 to 1000 gauss and is fabricated from a material selected from the group consisting of ferrite, ceramic and neodymium iron boron.

13. The combination of claim 7 wherein said magnets further have an outer diameter range from about 1.15 inch to about 2.0 inch, a hole diameter range from about 0.3 inch to about 0.7 inch, and a thickness range from about 0.07 inch to about 0.08 inch.

14. An eyeglass combination with permanent magnets for improvement of the eyes, said combination comprising:
    an eyeglasses frame; and
    a pair of bi-polar permanent magnets mounted directly on rims of said eyeglasses frame immediately in front of the eyes, each said magnet of said pair of magnets being a curved circular disk-shaped flexible permanent magnet with a plurality of uniformly distributed small holes, having alternating negative and positive poles throughout its area,
    said permanent magnets providing the therapeutic effect of increasing the flow and oxygen-carrying capacity of the blood circulating in the region of the eyes and activating the minerals in the cells and tissues of the eyes and surrounding region.

15. The combination of claim 14 wherein the eyeglasses are spectacles.

16. The combination of claim 14 wherein the eyeglasses are goggles.

17. The combination of claim 11 as wherein each said magnet in said pair of permanent magnets has a field strength in the range of 400 to 1000 gauss and is fabricated from a material selected from the group consisting of ferrite, ceramic and neodymium iron boron.

18. The combination of claim 14 wherein said magnets further have an outer diameter ranging from about 1.15 inch to about 2.0 inch, a multiple hole diameter ranging from 0.05 inch to 0.08 inch, and a thickness ranging from about 0.07 inch to about 0.08 inch.

* * * * *